United States Patent [19]

Kemme et al.

[11] 4,026,959
[45] May 31, 1977

[54] LOW TEMPERATURE ISOMERIZATION PROCESS FOR ISOPROPYLNAPHTHALENE (100 PERCENT SIEVE CATALYST)

[75] Inventors: Herbert Rudolph Kemme, Flemington; James Frederick Russ, North Brunswick, both of N.J.

[73] Assignee: American Cyanamid Company, Stamford, Conn.

[22] Filed: May 7, 1976

[21] Appl. No.: 684,214

[52] U.S. Cl. .................. 260/668 A; 260/671 R
[51] Int. Cl.² ................ C07C 5/28; C07C 15/24
[58] Field of Search .............. 260/668 A, 671 R

[56] References Cited

UNITED STATES PATENTS

| | | | |
|---|---|---|---|
| 3,251,897 | 5/1966 | Wise | 260/671 R |
| 3,845,149 | 10/1974 | Pietzsch et al. | 260/668 A |
| 3,886,223 | 5/1975 | Kemme et al. | 260/668 A |

*Primary Examiner*—Veronica O'Keefe
*Attorney, Agent, or Firm*—Charles J. Fickey

[57] ABSTRACT

A process for treating mixtures of isopropylnaphthalenes (IPN) obtained from any source and increasing the beta-isopropylnaphthalene content thereof by a batch or continuous isomerization reaction in the presence of a rare earth metal ammonium-exchanged, "Y Type" crystalline aluminosilicate catalyst. The process also includes disproportionation of higher alkylates of naphthalene, such as diisopropylnaphthalene, to increase the IPN content of said mixtures.

8 Claims, 5 Drawing Figures

FIG.1

LOW TEMPERATURE ISOMERIZATION PROCESS FOR ISOPROPYLNAPHTHALENE (100 PERCENT SIEVE CATALYST)

This invention relates to an improved process for isomerizing a mixture of alpha- and beta-isopropylnaphthalene to higher beta-isopropylnaphthalene content, as compared with processes of the prior art.

This invention provides a process which meets the above-described objective by providing a reaction mixture which contains from 96% to 98% beta-isopropylnaphthalene content based on the total isopropylnaphthalene content.

More particularly, it relates to a process for treating mixture of isopropylnaphthalenes (IPN) obtained from any source and increasing the beta-isopropylnaphthalene content thereof by a batch or continuous isomerization reaction in the presence of a rare earth metal ammonium-exchanged, "Y type" crystalline aluminosilicate catalyst. The process also includes disproportionation of higher alkylates of naphthalene, such as diisopropylnaphthalene, to increase the IPN content of said mixtures.

The terms "beta-isopropylnaphthalene content" and "beta-isopropylnaphthalene concentration" as used herein refer to the percentage of beta isopropylnaphthalene based on the total isopropylnaphthalene isomers present, that is, beta/alpha +beta × 100, as determined by conventional gas chromatographic procedures.

Alkylation of naphthalene with propylene in the presence of a synthetic crystalline aluminosilicate (zeolite) catalyst to obtain isopropylnaphthalenes is 100% (Wise U.S. Pat. No. 3,251,897). However, under the high temperature conditions necessary to achieve a high ratio of beta/alpha isomers in the isopropylnaphthalene, the yield of isopropylnaphthalene is reduced due to tar formation and polymerization of propylene. Formation of these by products also tends to shorten the life of the catalyst. On the other hand, if conditions of alkylation are such as to reduce tar formation, reduce propylene polymerization and prolong catalyst life such as by the use of low temperatures, the process is inefficient and results in low yields and low rates of production of the desired beta-isopropylnaphthalene. Thus, there is no method of which we are aware to efficiently produce isopropylnaphthalene in high yield and high beta isomer content and with economic use of catalyst by direct alkylation of naphthalene with propylene. This is true regardless of the catalyst used as far as we are aware.

There remains, therefore, a need for an economic process for the preparation of beta-isopropylnaphthalene in high yield and purity, from naphthalene and propylene.

We have now discovered an improved method for the preparation of beta-isopropylnaphthalene in high yield and purity whereby a mixture containing a low concentration of beta-isopropylnaphthalene, such as is obtained readily by low temperature alkylation of naphthalene with propylene by any known alkylation process, is converted by a process of isomerization over synthetic aluminosilicate catalysts to a mixture containing a very high concentration of beta-isopropylnaphthalene.

The process of the present invention converts mixtures of alpha- and beta- isopropylnaphthalenes (IPN) obtained from any source, i.e., whether obtained from alkylation using the catalyst system of this invention or an entirely different catalyst, conducted batchwise or continuously, with excellent conversion to a product having a high beta-isomer content and with prolonged catalyst life. However, it is preferable to operate continuously as hereinafter described. The reactions which occur may be described $$IPN + CH_3CH=CH_2 \underset{\leftarrow}{\overset{cat}{\rightarrow}} \text{diisopropylnaphthalenes (DIPN)}$$

$$DIPN + CH_3CH=CH_2 \underset{\leftarrow}{\overset{cat}{\rightarrow}} \text{triisopropylnaphthalenes (TIPN)}$$

$$TIPN + CH_3CH=CH_2 \underset{\leftarrow}{\overset{cat}{\rightarrow}} \text{higher alkylates (PIPN)}$$

In the batch type isomerization process naphthalene-free isopropylnaphthalene starting material is reacted with a rare earth ammonium-exchanged "Y" type alumino-silicate at a 25% to 50% catalyst loading at a temperature of from about 40° C. to about 200° C. in a suitable reaction vessel.

The term "catalyst loading" as used herein refers to the percent by weight of catalyst used in the total mixture. For example, a 25% catalyst loading refers to a mixture of 3 parts of isopropylnaphthalene and 1 part of catalyst.

Figure 1:
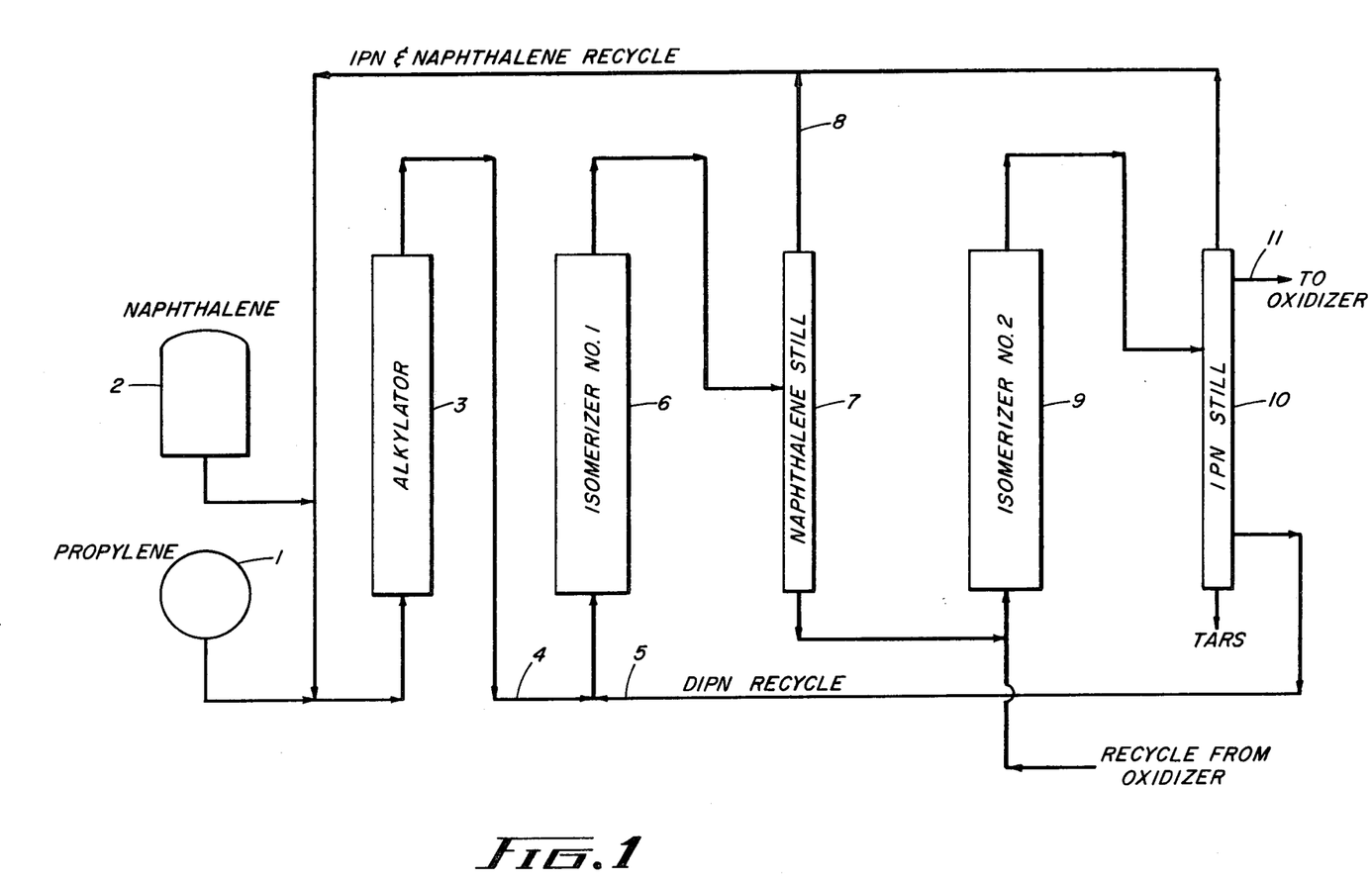

In the continuous mode of this invention propylene from tank 1 and naphthalene from tank 2 are continually metered to a packed bed alkylator 3 working at the lowest temperature required for prevention of excess tar formation. The alkylator discharge 4 is blended with recycled diisopropylnaphthalene 5 (DIPN) and alpha- and beta-isopropylnaphthalene isopropylnaphthalene and passed through a packed bed isomerizer 6 at about 150–260° C. where the alpha- and beta-isopropylnaphthalene mixture is isomerized to a 90–92% beta-isopropylnaphthalene content, and the by-product DIPN produced in the alkylator is disproportionated with naphthalene to produce additional isopropylnaphthalene. The discharge from isomerizer 6 may be fractionated immediately in still 7 and/or after a subsequent operation in a second isomerizer 9, to remove naphthalene 8 and isopropyl naphthalene which is recycled back to the alkylator 3 as shown in FIG. 1. The product of isomerizer 9 is fractionated in still 10. In the process of this invention we have found that it is important that the feed composition to the second isomerizer 9 contain essentially no naphthalene in order to obtain an isomerizer discharge having a 96–98% beta-isopropylnaphthalene content.

The removal of naphthalene from the feed composition stream to isomerizer 9 permits a shift of the equilibrium composition toward higher beta-isopropylnaphthalene values. For example, if the feed composition to the isomerizer contains approximately 60% by weight of naphthalene and the preferred catalyst system of this invention is employed over the temperature range of 80° to 150° C. the equilibrium beta-isopropylnaphthalene content of the isomerizer discharge ranges from 96.0% to 94.8%, respectively. However, if the feed composition contains no naphthalene under the same conditions the equilbrium beta-isopropylnaphthalene content of the isomerizer discharge ranges from 97.4% to 96.3%, respectively. Thus, by the process of this invention a significant increase is obtained in the beta-isopropylnaphthalene content of the discharge from the second isomerizer 9.

The preferred continuous process of the present invention contains two isomerization steps, the first isomerization conducted at a higher temperature and pressure than the second. The features which distinguish the process of the present invention from the prior art processes are: (1) the naphthalene distillation step before final isomerization, and (2) the presence of a low temperature atmospheric pressure final isomerization step. As shown in FIG. 1, the discharge from the first isomerizer is fractionated to remove naphthalene which is recylced back to the alkylator and the discharge is passed through the second isomerizer at low temperature and atmospheric pressure to enrich the beta-isopropylnaphthalene content to about 98%. The discharge from the second isomerizer is fractionated to remove DIPN, higher alkylates and tars. The DIPN is recycled to the first isomerizer and the isopropylnaphthalene product is passed on to the oxidation and cleavage steps by way of line 11.

While the alkylation reaction can be carried out with catalysts such as phosphoric acid, aluminum chloride, and the like, it is preferable to use the rare earth metal ammonium ion-exchanged "X" or "Y" type sodium-exchanged sieves required for the preparation of said catalysts are available from Union Carbide Corporation, the "Y" type sieve being the preferred type. Such catalysts are described in British Patent 1,155,282 and U.S. Pat. No. 3,251,897.

The preferred catalyst for the first isomerization step comprises an ammonium-exchanged "Y" type aluminosilicate containing rare earths supported on an amorphous alumina matrix. This catalyst contains about 7–14% w/w of active component based on analysis for rare earth oxides. Such catalysts are commercially available from American Cyanamid Company as Aerocat TS-150 and TS-260.

The preferred species of catalyst for the second isomerization step comprises an ammonium-exchanged 100% "Y" type aluminosilicate containing about 19.0% rare earths calculated as rare earth oxides.

Continuous isomerization with the catalyst systems of this invention is possible by partial replacement of catalyst by means of a catalyst recycle system. The recovered catalyst can be regenerated to its original activity by high temperature oxidation of the impurities therein.

Because of the relative inactivities of the prior art catalysts the relatively high temperatures required (200° C. to 260° C.) result in a feed stream for the oxidation-cleavage step which contains only about 90% to 92% beta-isopropylnaphthalene.

Figure 2:
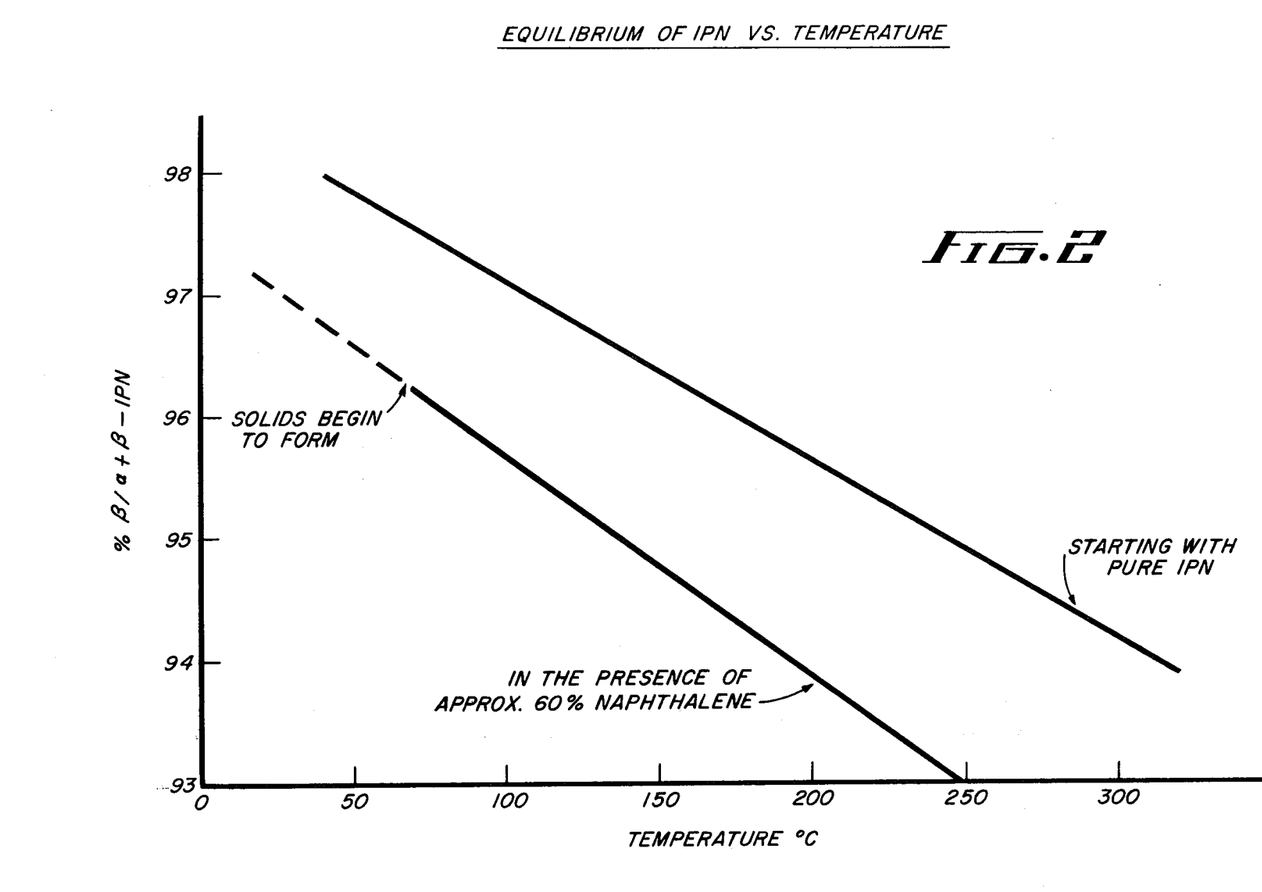
Figure 3:
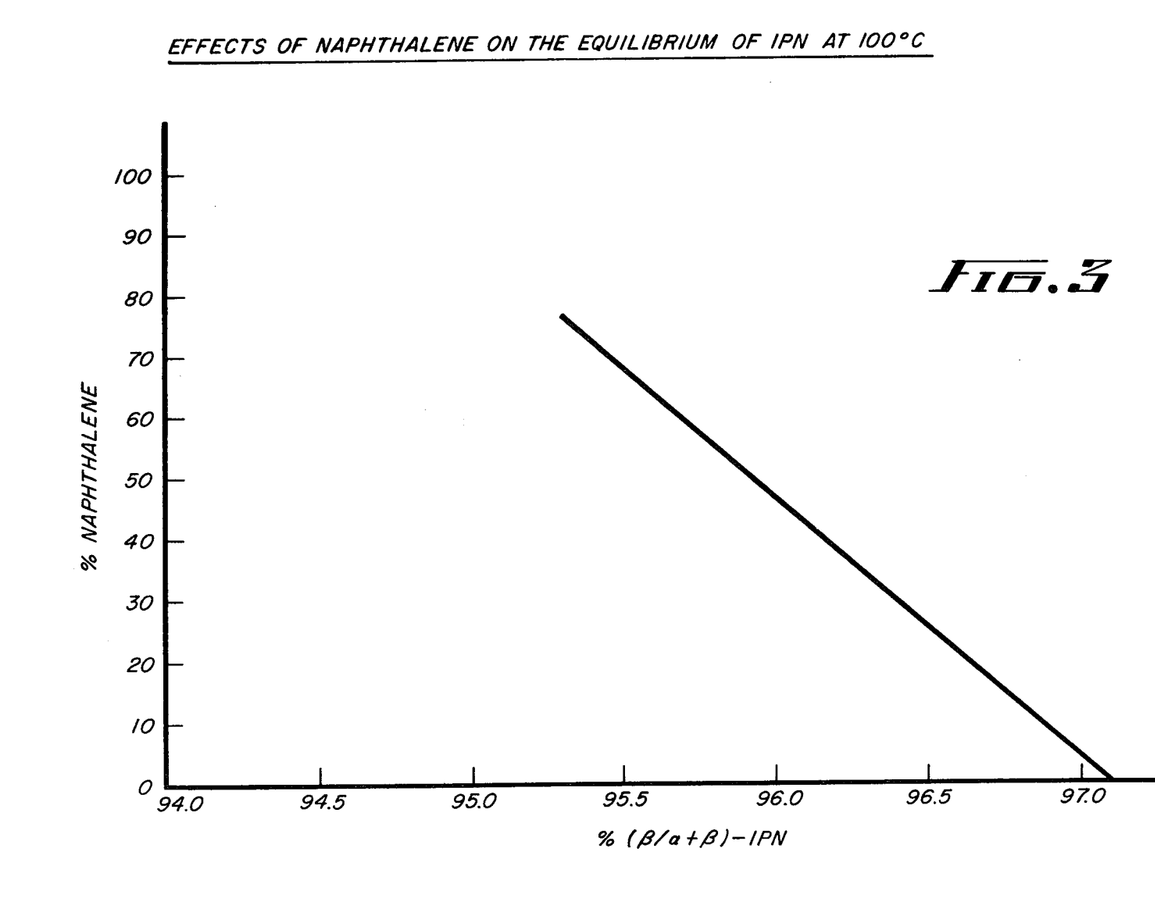
Figure 4:
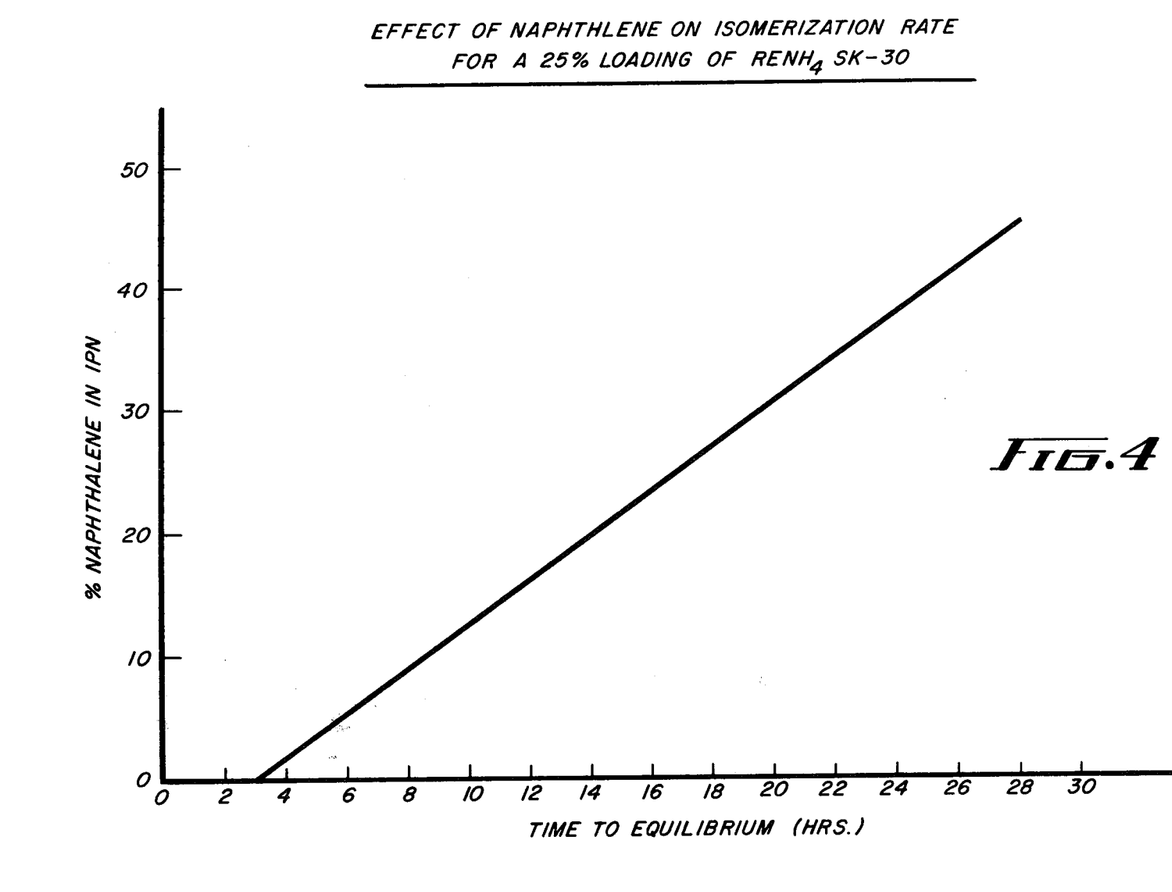

We have found that removal of excess naphthalene and isomerization at lower temperatures are critical factors in achieving the desired high beta-isomer content; high temperatures and high naphthalene content adversely affect the equilibrium between alpha- and beta-isopropylnaphthalene, as shown by FIGS. 2, 3 and 4.

The presence of either water, acidic or basic impurities in the feed to the isomerizers also adversely effects the rate of isomerization with these catalysts. Therefore it is vitally important that these impurities be removed by distillation or passing the feed to the isomerizers through caustic, alumina, or a molecular sieve such as Linde 4A; removal of water by distillation is preferred. It is also important that the catalyst be calcined to remove water. This may be carried out by heating the catalyst in an oven to about 500° C. overnight. This may be done by passing a stream of air through the oven, but it is preferable to carry it out under a pressure of a few pounds.

The feed mixture to be isomerized is preferably fed by means of a metering pump upwardly through fixed catalyst beds at a space velocity (S.V.) of from 0.1 to 4.0 hour$^{-1}$. (Space velocity = ft.$^3$ of aromatic material/ft.$^3$ of catalyst bed-hour). If the S.V. is less than about 0.1 hour$^{-1}$, the reaction is not economical and requires large scale equipment, if greater than about 4 hour$^{-1}$ the degree of conversion is too low. It is preferable to operate at a S.V. of 0.3 hour$^{-1}$ to 1.0 hour$^{-1}$.

Positive pressure is necessary to maintain flow through the alkylator and isomerizers and to prolong catalyst life. Pressures of 200 psi to 500 psi are preferred for the alkylator and the first isomerizer. The second isomerizer is preferably operated at atmospheric pressure or slightly above.

The feed stock to the first isomerizer is a mixture containing naphthalene, alpha- and beta-isopropylnaphthalene, diisopropylnaphthalenes and propylene. In fact the naphthalene/propylene ratio is an important factor in the first isomerization step since low naphthalene/propylene ratios favor formation of high concentrations of diisopropylnaphthalene while high naphthalene/propylene ratios lead to low reaction efficiency and decreased beta isopropylnaphthalene content. Therefore, the feed stock to the first isomerizer should contain from about 1 to 10 equivalents of naphthalene per equivalent of propylene, preferably it should contain from about 2 4 4 equivalents of naphthalene per equivalent of propylene, taking all alkylated and unalkylated species into account.

The temperature of the first isomerization step should be between 150° and 260° C. Temperatures above 260° C. result in excessive tar formation and shortened catalyst life due to catalyst fouling. Below about 150° C. the isomerization reaction is too slow. The preferred temperature range is about 180° C. to 240° C. As the reaction temperature is increased it is desirable to increase the space velocity, thereby minimizing tar formation and increasing catalyst life. A combination of low temperature and low space velocity is preferred.

The feed stock to the second isomerizer is a mixture of DIPN, PIPN, alpha- and beta-isopropylnaphthalene plus residual traces of naphthalene (1% of less) carried over from the naphthalene still. In the second isomerization step the reduced naphthalene content of the feed stock favors the conversion of any residual alpha isopropylnaphthalene to the beta isomer.

The temperature of the second isomerization step should be between 70° C. and 175° C., preferably between 90° C. and 110° C.

To the best of our knowledge the effect of the removal of naphthalene on increasing the rate of isomerization and shifting the equilibrium in favor of high beta content have not been disclosed to date. To the best of our knowledge there are no patents in existence which claim the process of this invention.

The following examples illustrate the process of this invention.

EXAMPLE 1

The following example illustrates the preparation of the rare earth ammonia-exchanged catalyst species of this invention which is referred to hereinafter as RENH$_4$SK-30.

The procedure of Example 5 of British Patent 1,155,282, which is hereby incorporated by reference, is followed. Analysis showed 18.5% RE$_2$O$_3$, and 1.4% Na$_2$O, both on a dry basis. No ammonia determination was made on this particular catalyst.

This catalyst may be diluted with alumina or silica for use in the alkylation step, or first isomerization step.

EXAMPLE 2

The following example illustrates the preparation of a rare earth sodium-exchanged catalyst which is used in a comparison experiment.

The procedure of Example 3 of British Patent 1,155,282, which is hereby incorporated by reference, is followed. Analysis showed 17.46% RE$_2$O$_3$, and 3.34% Na$_2$O, both on a dry basis. This catalyst is referred to hereinafter as RENaSK-30.

EXAMPLE 3

The following experiment illustrates a batch process for the isomerization step.

To a suitable reaction vessel is added 300.0 g of caustic-washed isopropylnaphthalene which analyzed as follows:

87.26 Beta-isopropylnaphthalene, 12.09% alpha-isopropylnaphthalene and 0.54% naphthalene. The beta-isopropylnaphthalene content on the basis of total isopropylnaphthalenes is 87.8%. To the vessel is also added 1000.0 grams of the catalyst of Example 1 which had been passed through a No. 20 sieve. The reaction vessel is blanketed with nitrogen, heated to 100° 120° C. and sampled periodically to determine the beta-isopropylnaphthalene content. The results obtained are shown in Table I.

Table I

| Elapsed Time (Hrs.) | $\frac{\beta}{\alpha+\beta} \times 100$ |
|---|---|
| 0 | 87.8% |
| 1 | 96.5 |
| 2 | 97.1 |
| 3 | 96.7 |
| 5 | 96.7 |
| 7 | 96.6 |

EXAMPLE 4

The following experiments demonstrate the enhanced activity of the catalyst of this invention on the rate of isomerization when compared to the corresponding sodium-ion exchanged catalyst and the catalyst diluted with silica and alumina.

The procedure of Example 3 is used using the catalysts of Example 1 2, 2, and the catalyst of Example 1 diluted with an equal amount of a mixture of alumina and silica; three parts by weight of starting isopropylnaphthalene are used to one part by weight of "as is" (uncalcined) catalyst. The rate of increase of beta-isomer content in the first hour at 100° C. was determined. The results are shown in Table II.

Table II

| Catalyst | Change in Beta-Isomer Content After One Hour |
|---|---|
| RE NH$_4$ SK-30 | + 7.6% |
| RE Na SK-30 | + 3.5% |
| 50/50 RE NH$_4$ Sk-30/Al$_2$O$_3$—SiO$_2$ | 0 |

EXAMPLE 5

The effect of the percentage of naphthalene in the starting material on the isomerization rate and the equilibrium beta-IPN content is shown by the following experiment wherein the percentage of naphthalene in the starting material is varied for isomerizations conducted at 100° C. using 30.0 grams of starting material per gram of catalyst of Example 1.

The results as shwon in Table III and FIGS. 3 and 4 illustrate the retarding effect of naphthalene on the isomerization reaction and the beta-IPN equilibrium content.

TABLE III

| % Naphthalene in Starting Material | Hours required to Attain Equilibrium | $\frac{\beta}{\alpha+\beta} \times 100$ |
|---|---|---|
| 0.0 | 3.0 | 97.1 |
| 16.5 | 9.6 | 96.9 |
| 25.0 | 17.0 | 96.6 |
| 39.0 | 26.0 | 95.8 |
| 64.0 | 55.0 | 95.6 |

EXAMPLE 6

The effect of the naphthalene content of the feed composition on the equilibrium composition of the isomerizer discharge is demonstrated by the following experiments wherein caustic-washed distilled isopropylnaphthalene (Comp. A) of 88.8% beta isomer content, based on total alpha + beta content, is isomerized in the range of 40° C. to 200° C. and compared under similar conditions to feed Composition B which contains approximately 60% naphthalene by weight. The results as shown in Table IV and FIG. 2 illustrate the fact that Composition B gives consistently lower equilibrium beta-isopropylnaphthalene values than those obtained at the same temperature with the essentially naphthalene-free Composition A. In all cases three parts of Composition A or B per part of catalyst from Example 1 are used.

Table IV

| Temp. ° C. | Comp. A | Comp. B | Remarks |
|---|---|---|---|
| 40 | 98.0 | — | Comp. B solidifies at 40° C |
| 80 | 97.4 | 96.0 | |
| 100 | 97.1 | 95.7 | |
| 120 | 96.8 | 95.3 | |
| 150 | 96.3 | 94.8 | |
| 200 | 95.7 | 93.9 | |

EXAMPLE 7

Isomerization of caustic-washed distilled isopropylnaphthalene was carried out at the temperatures and for the times indicated in Table V with 100% molecular sieve catalyst described in Example 1, using 3.0 grams of isopropylnaphthalene per gram of catalyst. The starting isopropylnaphthalene contained 88.8% beta-isopropylnaphthalene based on total (alpha- + beta-) isomer content.

Table V

| Experiment | Temp. (°C) | % Beta-Isopropylnaphthalene in Product Based On Isopropylnaphthalene Content After Isomerization For the Hours Indicated | | | |
|---|---|---|---|---|---|
| | | 0.25 Hr. | 0.50 Hr. | 1.0 Hr. | 2.0 Hrs. |
| 1 | 70 | 89.6 | 90.3 | 91.6 | 93.8 |
| 2 | 80 | 90.5 | 92.0 | 94.5 | 96.8 |
| 3 | 90 | 91.4 | 93.5 | 95.6 | 97.0 |
| 4 | 100 | 92.0 | 94.6 | 96.3 | 96.9 |
| 5 | 120 | 93.5 | 96.0 | 96.6 | 96.7 |
| 6 | 150 | 96.1 | 96.3 | 96.3 | 96.4 |
| 7 | 200 | 95.9 | 95.9 | 95.9 | 96.0 |

These results support the broad temperature range 70°–175° C., and the preferred temperature range of 90°–110° for the second isomerization step.

EXAMPLE 8

The following experiments illustrate that the rate of isomerization to the beta-isomer increases as the sieve content of the catalyst increases and as the water content is reduced. The results obtained are shown in Table VI. All experiments were conducted at 100° C using the procedure of Example 3, and the catalyst of Example 1 with alumina as diluent.

Table VI

| Experiment | Sieve Content (%) | Rate Per Hr. (%) | Remark | Notebook No. |
|---|---|---|---|---|
| 1 | 7 | 0.064 | "As in" catalyst | R 7686–133 |
| 2 | 14 | 0.13 | " | R 8308–149 |
| 3 | 77 | 1.30 | " | R 8308–146 |
| 4 | 100 | 14.40 | " | R 8308–110 |
| 5 | 100 | 55.00 | Freshley calcined catalyst | R 8308–166 |

*$\beta/\alpha + \beta$ versus time for zero-order part of reaction

EXAMPLE 9

Figure 5:
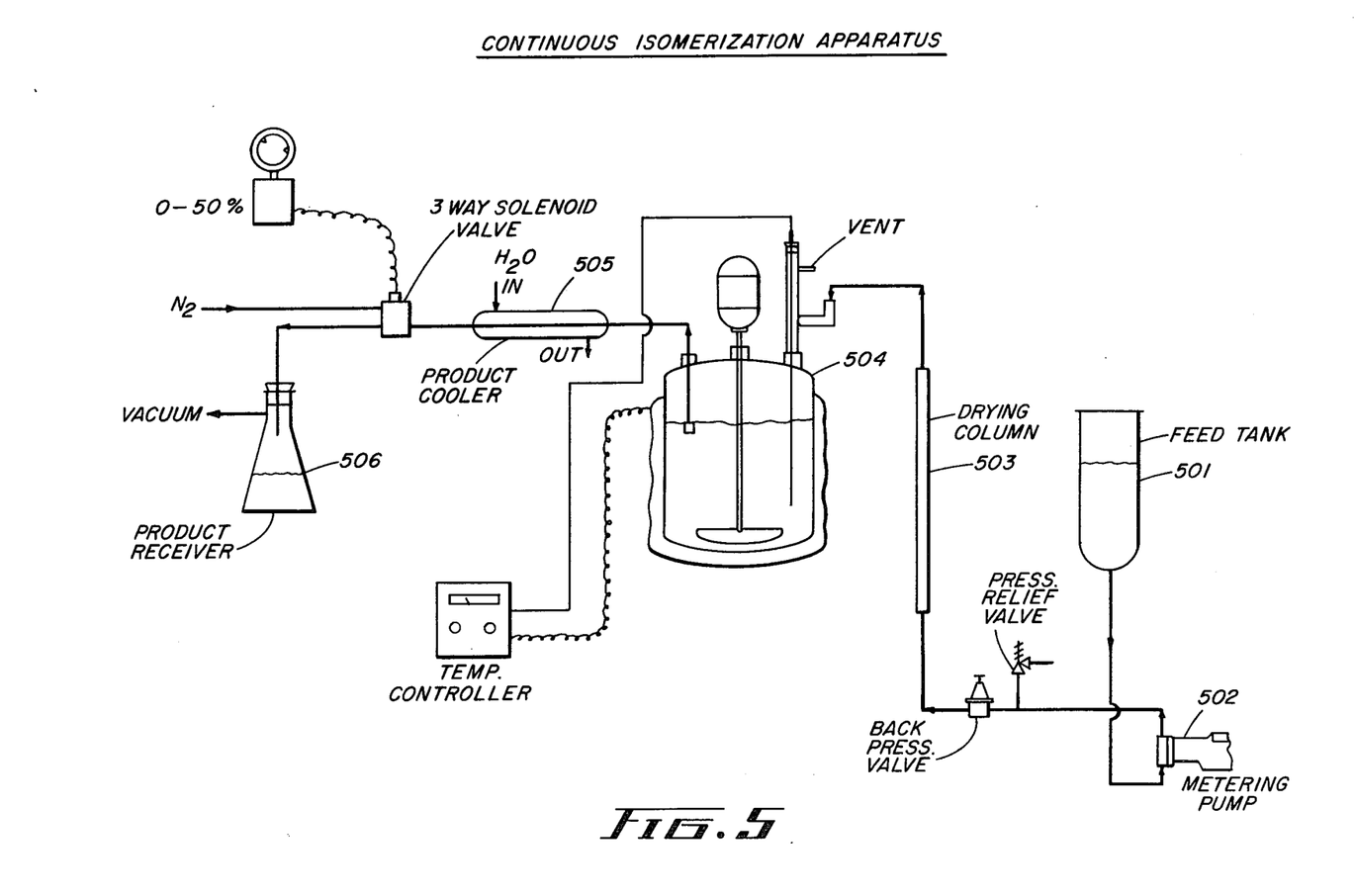

The following example illustrates the operation of the process of this invention in a continuous mode using a small bench scale reaction system as shown in FIG. 5. The mixture to be isomerized is charged to a feed tank 501 where it is pumped through a metering pump 502 upwardly into a drying column 503 packed with Linde 4A drying sieves. The discharge from the drying column is then passed into the reactor tank 504 (isomerizer) where it is stirred with the catalyst of Example 1 using 3 grams of isopropylnaphthalene feed per gram of catalyst with the feed and take-off rates adjusted to allow a two hour residence time in 504. The discharge from 504 is then passed through a heat exchanger 505 where it is cooled and discharged at slightly reduced pressure to a product receiver 506 where it is sampled for analysis.

The catalyst and feed isopropylnaphthalene (94.97% beta isomer) is charged to 504 and the reactor is heated to 80° C. and held at 80° C. for 2 hours. At the end of this period the material in 504 is sampled and found to have a beta isomer content of 97.4The temperature is then increased, feed is metered continuously into the reactor at about 200 ml. per hour and the beta-isomer content of the product in 506 is determined periodically.

The results obtained are shown below in Table VII.

Table VII

| Total Hours Elapsed | Temp. °C. | Feed Added (ml.) | Product Collected (ml.) | + (%) | Remarks |
|---|---|---|---|---|---|
| 0 | 80 | 0 | 0 | 94.97 | |
| 2 | 80 | 0 | 0 | 97.4 | Increased to 87° C |
| 16½ | 87 | 3100 | 3100 | 97.0 | Increased to 97° C |
| 22¼ | 97 | 4400 | 4400 | 97.0 | |
| 25¼ | 97 | 4000 | 5000 | 96.9 | Increased to 100° C |
| 39 | 100 | 7670 | 7670 | 96.8 | Increased to 105° C |
| 45½ | 105 | 8850 | 8850 | 96.7 | |

The above results show that the isomerization of feed composition which contains 94.97 beta-isomer content results in rapid increase in the beta-isomer content to about 96.7–97.0% and is maintained at this level over more than 45 hours of continuous operation.

EXAMPLE 10

After a temperature of 105° C. had been reached in Example 9 the temperature was lowered to 100° C. and 15% by weight of the catalyst was removed and replaced with fresh catalyst. The reaction was continued at 100° C. with a change of only 0.1%(96.7% to 96.6% in the equilibrium beta-isopropylnaphthalene content of the product. This example demonstrates the ability to maintain high catalytic activity at a constant temperature by the removal and replacement of old catalyst with fresh catalyst.

EXAMPLE 11

To a suitable reaction vessel was charged 300 grams of a composition listed in Table VIII under zero time and 100 g. of the catalyst of Example 1. The mixture was heated and stirred at 100° C. and periodically samples were removed and analyzed. The results obtained are shown in Table VIII.

Table VIII

| Time (Hrs.) | Percent by weight | | | | | |
|---|---|---|---|---|---|---|
| | Napthalene | $\beta$-IPN | $\alpha$-IPN | IPEN[a] | DIPN | $\frac{\beta}{\beta+\alpha}$ |
| 0.0 | 0.182 | 75.870 | 4.20 | 0.028 | 18.052 | 94.75 |
| 0.5 | 0.535 | 74.762 | 2.244 | N.D.[b] | 19.679 | 97.09 |
| 1.0 | 0.878 | 72.580 | 2.159 | " | 20.15 | 97.11 |
| 1.5 | 1.132 | 71.646 | 2.059 | " | 20.56 | 97.21 |
| 2.2 | 1.591 | 69.224 | 2.018 | " | 21.78 | 97.16 |
| 5.5 | 2.383 | 66.253 | 1.867 | " | 23.39 | 97.25 |
| 7.5 | 2.692 | 65.077 | 1.792 | 0.044 | 24.17 | 97.32 |

[a]IPEN = tetraline
[b]N.D. = Not Determined

This example illustrates the fact that increases in the DIPN content do not affect the equilibrium beta-isopropylnaphthalene value.

What is claimed is:

1. A process for increasing the beta-isopropylnaphthalene content of a mixture containing essentially naphthalene, alpha- and beta-isopropylnaphthalene and diisopropylnaphthalene, which comprises contacting said mixture with a diluted rare earth metal ammonium-exchanged, synthetic, crystalline "Y" type allumino-silicate catalyst at a temperature of from about 150° C to 260° C., with a space velocity of from about 0.1 to 4 hour$^{-1}$, at a gauge pressure of from about 200 psi to 500 psi, said mixture having about 1 to 10 equivalents naphthalene per equivalent of propylene, removing residual naphthalene from the reaction product, and further contacting the naphthalene-free product with a rare earth metal ammonium-exchanged, 100% synthetic, crystalline "Y" type aluminosilicate catalyst at a temperature of from about 70° C. to 175° C., at substantially atmospheric pressure, and recovering the product therefrom.

2. The process of claim 1 wherein the diluent is alumina.

3. The process of claim 1 wherein the diluent is silica.

4. A process for increasing the beta-isopropylnaphthalene content of a mixture containing essentially naphthalene, alpha- and beta-isopropylnaphthalene and diisopropylnaphthalene, which comprises contacting said mixture with a diluted rare earth metal ammonium-exchanged, synthetic, crystalline "Y" type aluminosilicate catalyst at a temperature of from about 180° C. to 240° C., with a space velocity of from about 0.3 to 1.0 hour$^{-1}$, at a gauge pressure of from about 200 psi to 500 psi, said mixture having about 2 to 4 equivalents of naphthalene per equivalent of 280° propylene, removing residual naphthalene from the reaction product, and further contacting the naphthalene-free product with a rare earth metal exchanged, 10% synthetic, crystalline "Y" type aluminosilicate catalyst at a temperature of from about 90° C. to 110° C., at substantially atmospheric pressure and recovering the product therefrom.

5. The process of claim 4 wherein the diluent is alumina.

6. The process of claim 4 wherein the diluent is silica.

7. A process for increasing the beta-isopropylnaphthalene content of a mixture containing essentially naphthalene, alpha- and beta-isopropylnaphthalene and diisopropylnaphthalene, which comprises separating the naphthalene from said mixture and contacting the essentially naphthalene-free mixture with a rare earth metal ammonium-exchanged 100% synthetic, crystalline "Y" type aluminosilicate catalyst at a temperature of from about 40° C. to 200° C. at substantially atmospheric pressure, and recovering the product therefrom.

8. A process according to claim 7 wherein from 1 to 3 parts by weight of isopropylnaphthalene mixture is used per part by weight of catalyst.

* * * * *

UNITED STATES PATENT OFFICE
CERTIFICATE OF CORRECTION

Patent No. 4,026,959            Dated May 31, 1977

Inventor(s) HERBERT RUDOLPH CONRAD KEMME ET AL.

It is certified that error appears in the above-identified patent and that said Letters Patent are hereby corrected as shown below:

Claim 4, Column 10, line 3, "10%" should read -- 100% --.

Signed and Sealed this

Twenty-seventh Day of November 1979

[SEAL]

Attest:

RUTH C. MASON
Attesting Officer

LUTRELLE F. PARKER
Acting Commissioner of Patents and Trademarks